(12) United States Patent
Zhang et al.

(10) Patent No.: US 11,737,655 B2
(45) Date of Patent: Aug. 29, 2023

(54) ENDOSCOPE LOCKING DEVICE

(71) Applicant: Shenyang Shengshi Medical Technology Co., Ltd., Shenyang (CN)

(72) Inventors: Lijun Zhang, Shenyang (CN); Tao Zhu, Shenyang (CN); Wei Gao, Shenyang (CN)

(73) Assignee: SHENYANG SHENGSHI MEDICAL TECHNOLOGY CO., LTD., Liaoning (CN)

( * ) Notice: Subject to any disclaimer, the term of this patent is extended or adjusted under 35 U.S.C. 154(b) by 493 days.

(21) Appl. No.: 16/346,971

(22) PCT Filed: Jun. 5, 2017

(86) PCT No.: PCT/CN2017/087189
§ 371 (c)(1),
(2) Date: May 2, 2019

(87) PCT Pub. No.: WO2018/082301
PCT Pub. Date: May 11, 2018

(65) Prior Publication Data
US 2020/0060515 A1 Feb. 27, 2020

(30) Foreign Application Priority Data

Nov. 2, 2016 (CN) .......................... 201621174142.0

(51) Int. Cl.
*A61B 1/00* (2006.01)
*A61B 1/307* (2006.01)
*A61B 1/04* (2006.01)

(52) U.S. Cl.
CPC ........ *A61B 1/00135* (2013.01); *A61B 1/0014* (2013.01); *A61B 1/04* (2013.01); *A61B 1/307* (2013.01)

(58) Field of Classification Search
CPC ... A61B 1/0014; A61B 1/00135; A61B 1/307; A61B 1/04; A61B 17/00; A61B 1/00147;
(Continued)

(56) References Cited

U.S. PATENT DOCUMENTS 5,456,673 A * 10/1995 Ziegler .............. A61B 17/3462
604/533
5,792,045 A * 8/1998 Adair ................. A61B 1/00128
600/125

(Continued)

FOREIGN PATENT DOCUMENTS

CN 100569175 C * 12/2009
CN 101964263 A 2/2011
(Continued)

OTHER PUBLICATIONS

International Patent Application No. PCT/CN2017/087189; Int'l Written Opinion and Search Report; dated Aug. 25, 2017; 13 pages.

*Primary Examiner* — Anh T Nguyen
*Assistant Examiner* — Sung Ham
(74) *Attorney, Agent, or Firm* — Caesar Rivise, PC

(57) ABSTRACT

An endoscope locking device comprises: a pedestal, a lock buckle and an elastic element, the pedestal is provided with a slot for mounting the lock buckle, the lock buckle is provided with an oblong hole in the center, and the lock buckle is mounted within the slot of the pedestal, and the lock buckle may reciprocate within the slot; and the lock buckle and the pedestal are elastically connected by the elastic element. The endoscope is fixed by using the elasticity of the elastic rubber ring to the endoscope locking device formed by the lock buckle and the pedestal.

6 Claims, 6 Drawing Sheets

(58) Field of Classification Search
CPC ..... A61B 1/00; A61B 1/00066; A61B 1/0052; A61B 1/0057
See application file for complete search history.

(56) References Cited

U.S. PATENT DOCUMENTS

| | | | | |
|---|---|---|---|---|
| 6,086,530 | A * | 7/2000 | Mack | A61B 1/00135 600/121 |
| 6,132,402 | A * | 10/2000 | Tessmann | A61M 5/344 285/305 |
| 6,595,439 | B1 | 7/2003 | Chen | |
| 2006/0009677 | A1 * | 1/2006 | Lehmann | A61B 1/00126 600/104 |
| 2007/0077827 | A1 * | 4/2007 | Bonde | A61B 18/1485 439/745 |
| 2016/0045100 | A1 * | 2/2016 | Eto | A61B 1/00087 600/106 |
| 2016/0120395 | A1 * | 5/2016 | Qi | A61B 1/00135 600/123 |

FOREIGN PATENT DOCUMENTS

| | | |
|---|---|---|
| CN | 102119847 A | 7/2011 |
| CN | 102283684 A | 12/2011 |
| CN | 102395308 A | 3/2012 |
| CN | 103445748 A | 12/2013 |
| CN | 105816208 A | 8/2016 |
| CN | 106361388 A | 2/2017 |
| CN | 106618448 A | 5/2017 |
| JP | 2006-009395 A | 1/2006 |
| JP | 2013-155932 A | 8/2013 |
| WO | WO 2007/115225 A2 | 10/2007 |

\* cited by examiner

ENDOSCOPE LOCKING DEVICE

CROSS-REFERENCE TO RELATED APPLICATIONS

This application is the National Stage of International Application No. PCT/CN2017/087189, filed on Jun. 5, 2017, which claims priority to Chinese Patent Application No. 201621174142.0, filed on Nov. 2, 2016, both of which are hereby incorporated by reference in their entireties.

TECHNICAL FIELD

The present application relates to an endoscope sheath, and particularly relates to an endoscope locking device.

BACKGROUND ART

The endoscopes used for the surgeries on urinary system and bladder are generally defined as precise instrument, and have high prices and high costs for maintenance and cleaning, and too frequent cleaning shortens the service life of the instrument. The actual surgeries always employ a disposable endoscope sheath to insert into a human body, to not contact the endoscope directly with the human body, to avoid the endoscope from being contaminated by bacteria. After the surgery has ended, the disposable endoscope sheath can be discarded, and the endoscope is merely required to be simply rinsed.

The firm connecting between the endoscope and the sheath is a precondition that ensures a successful surgery. The patent CN201310430412.4 discloses a disposable locking structure for an endoscope sheath, wherein the structure comprises a sheath, a middle layer sleeve, a locking sleeve, and a port between the sheath and the endoscope, and the middle layer sleeve and the locking sleeve nest the sheath at the port to lock the endoscope; the port between the sheath and the endoscope is of a shape wherein the left and right ends are wide and the upper and lower ends are narrow, and the port is provided with a positioning slot; one end of the sheath is provided with a round positioning pin; the middle layer sleeve is provided with a safety switch; and one end of the locking sleeve is provided with two blocking edges at the circle, and the other end of the locking sleeve is provided with a positioning pin. After the locking device has locked, the rotation of the endoscope is usually in the range of 70-110°. The device has a complicated structure, and the assembling and detaching of the endoscope are tedious.

SUMMARY OF THE DISCLOSURE

An object of the present application is to provide an endoscope locking device, to solve the problems of complicated structures of locking devices and of tedious assembling and detaching of endoscopes.

In order to achieve the above object, the present application discloses an endoscope locking device, wherein the endoscope locking device comprises: a pedestal, a lock buckle and an elastic element;

the pedestal is provided with a slot for mounting the lock buckle, the lock buckle is provided with an oblong hole in a center, and the lock buckle is mounted within the slot of the pedestal, and the lock buckle may reciprocate within the slot;

the lock buckle and the pedestal are elastically connected by the elastic element.

Optionally, the slot of the pedestal is closed at the two sides, to ensure the position of the lock buckle in the slot, and is open at the two ends, to enable the lock buckle to reciprocate.

Optionally, a radius of one end of the oblong hole of the center of the lock buckle is equal to a radius of an endoscope, and a radius of the other end is greater than the radius of the endoscope, to ensure the tight clipping of the endoscope without scratching the surface of the endoscope.

Optionally, the elastic element is an elastic rubber ring, to facilitate the installation and replacing and reduce the cost.

Optionally, the pedestal is provided with a groove for mounting the elastic rubber ring.

Optionally, the lock buckle is of a cuboidal sheet structure, wherein one end of the lock buckle is a step having a circular arc transition, the other end is a circular arc, the circular arc end is provided with a protrusion, and the protrusion is provided with a groove for mounting the elastic rubber ring.

Optionally, the elastic rubber ring is mounted in the groove of the lock buckle and the groove of the pedestal, and the lock buckle and the pedestal are elastically connected.

Optionally, the pedestal is of a funnel shape having a central hole, the pedestal comprises a top portion and a neck portion, the top portion of the central hole of the pedestal is a connector for mounting the endoscope, the connector is provided with a round hole therewithin, and a diameter of the round hole is greater than a diameter of the endoscope.

Optionally, a lock buckle cap is mounted on the step of the lock buckle, to facilitate the pressing operation.

Optionally, an endoscope sheath is provided, wherein the endoscope sheath comprises the endoscope locking device, a three-way connector, a four-way connector, a locking screw, a valve, a probe tube, a probe head, a thick pipe, a thin pipe and a lock buckle cap;

the endoscope locking device is connected to a first connecting end of the three-way connector, a second connecting end of the three-way connector is an instrument entrance, a third connecting end of the three-way connector is connected to a connecting end of the four-way connector, one end of the probe tube is connected to another connecting end of the four-way connector, and the probe head is connected to the other end of the probe tube.

Preferably, the radiuses of the oblong hole of the center of the lock buckle are R6.2 mm and R5.3 mm, the total length of the oblong hole is 16.6 mm, the grooves on the lock buckle and the pedestal for mounting the elastic rubber ring are of a circular arc shape, the radius of the circular arc of the groove on the lock buckle is R1 mm, and the radius of the circular arc of the groove on the pedestal is R1.2 mm. The thickness of the lock buckle is 1.2 mm, and the thickness of the slot for mounting the lock buckle on the pedestal is 1.4 mm.

In the present application, the endoscope is fixed by using the elasticity of the elastic rubber ring to the endoscope locking device formed by the lock buckle and the pedestal, the endoscope locking device has the characteristic of a simple structure and the characteristic that the assembling and detaching of the endoscope are simple, which can improve the surgery efficiency.

The other characteristics and advantages of the present application will be described in the subsequent description, and partially become apparent from the description or be understood by the implementation of the present application. The objects and the other advantages of the present application can be implemented and obtained from the structures particularly illustrated in the written description, claims and drawings.

BRIEF DESCRIPTION OF DRAWINGS

The drawings are merely for the purpose of illustrating the particular embodiments, and are not considered as limitation to the present application. Throughout the drawings, the same reference signs denote the same elements.

Figure 1:
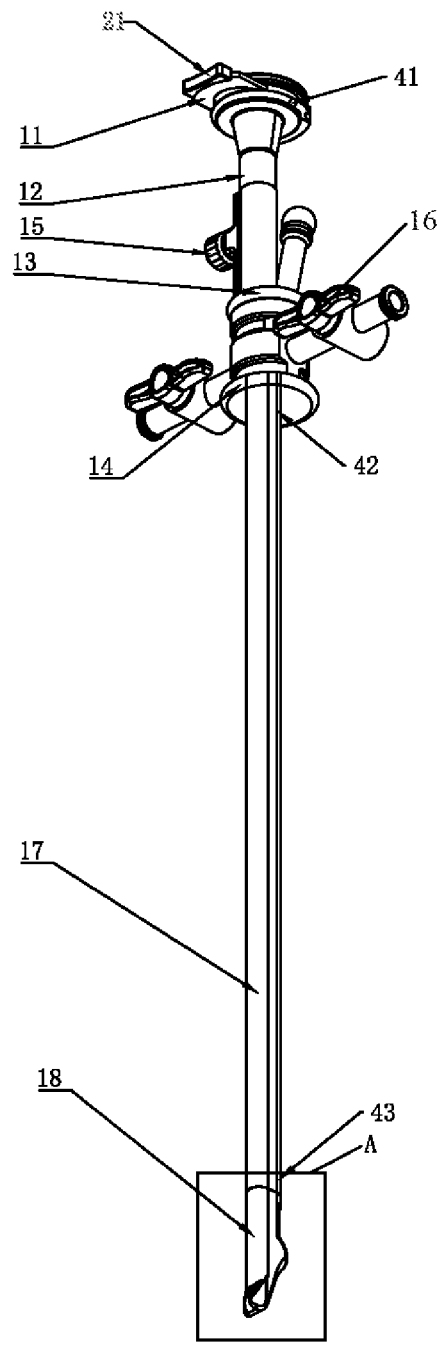
FIG. 1 is a schematic diagram of the overall structure of the present application.
Figure 2:
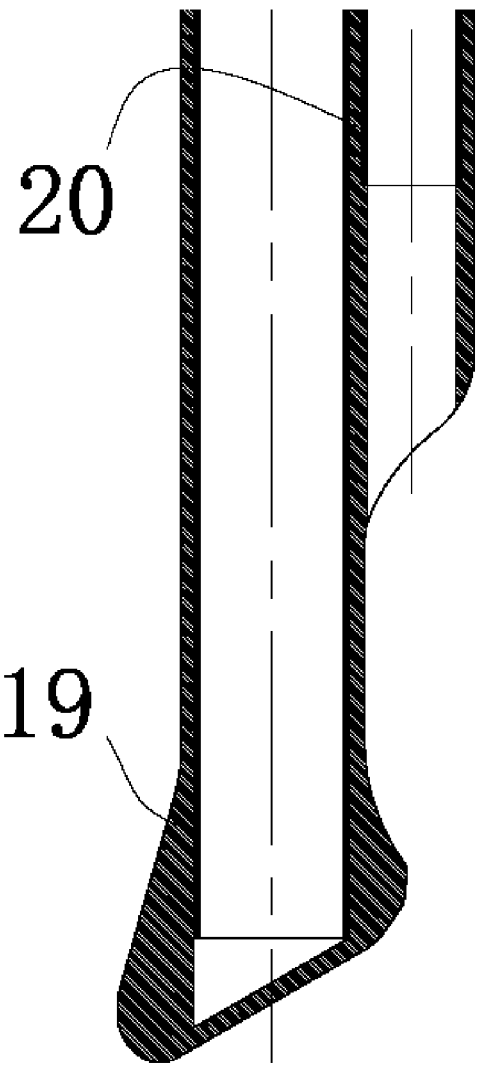
FIG. 2 is a partial enlarged view of the A in the overall structure of the present application.

The reference numbers in the drawings: 11—lock buckle, 12—pedestal, 13—three-way connector, 14—four-way connector, 15—locking screw, 16—valve, 17—probe tube, 18—probe head, 19—thick pipe, 20—thin pipe, 21—lock buckle cap; 131—first connecting end, 132—second connecting end, and 133—third connecting end, 41—elastic element, 42—one end of the probe tube, 43—other end of the probe tube, 52—oblong hole, 53—step, 54—protrusion, 55—groove, 57—connecting end of the four-way connector, 58—another connecting end of the four-way connector.

DETAILED DESCRIPTION

The preferable embodiments of the present application will be particularly described below with reference to the drawings. The drawings form a portion of the present application, and are for explaining the principle of the present application together with the embodiments of the present application.

The present application discloses an endoscope locking device. As shown in FIG. 1, the endoscope locking device comprises: a lock buckle 11, a pedestal 12, an elastic element 41, a three-way connector 13, a four-way connector 14, a locking screw 15, a valve 16, a probe tube 17, a probe head 18, a thick pipe 19, a thin pipe 20 and a lock buckle cap 21. And the lock buckle 11 and the pedestal 12 are elastically connected by the elastic element 41.

The lock buckle 11 is mounted on the pedestal 12, the pedestal 12 is connected to a first connecting end 131 of the three-way connector 13, a second connecting end 132 of the three-way connector 13 is an instrument entrance, a third connecting end 133 of the three-way connector 13 is connected to a connecting end of the four-way connector 14, one end 42 of the probe tube 17 is connected to another connecting end of the four-way connector 14, and the probe head 18 is connected to the other end 43 of the probe tube 17.

The locking device is of a snap ring type, and the lock buckle 11 is elastically connected to the pedestal 12 via an elastic rubber ring.

Figure 3:
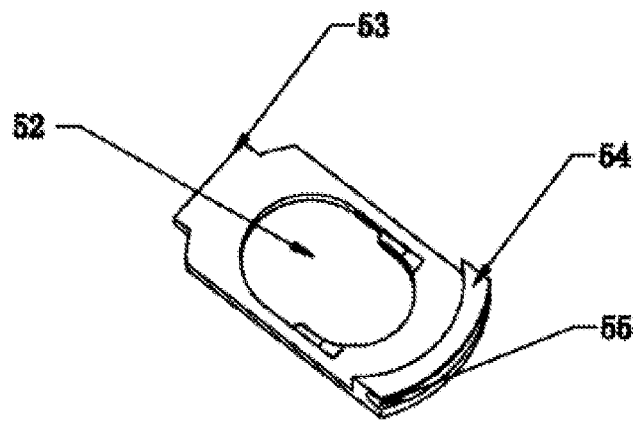
FIG. 3 is a structural diagram of the lock buckle of the present application.

As shown in FIG. 3, the lock buckle 11 is of a cuboidal sheet structure, One end of the lock buckle 11 is a step 53 having a circular arc transition, and a lock buckle cap 21 is mounted on the step, for pressing the lock buckle, to facilitate the operation. The other end of the lock buckle 11 is a circular arc, and the lock buckle 11 is provided with an oblong hole 52 in the center, which is the central hole. The circular arc end of the lock buckle 11 is provided with a protrusion 54, the protrusion is provided with a groove 55 for mounting the elastic rubber ring, the protrusion is of a circular arc shape, and the circular arc shape matches with the shape of the position of the pedestal 12 where the lock buckle 11 is mounted, to facilitate the lock buckle 11 mounting on the pedestal 12. The radius of the end of the central hole adjacent to the circular arc end of the lock buckle 11 is equal to the radius of the endoscope, whereby the endoscope can be fastened without scratching the surface of the endoscope, and the radius of the other end of the central hole is greater than the radius of the endoscope, to facilitate the mounting.

Figure 4:
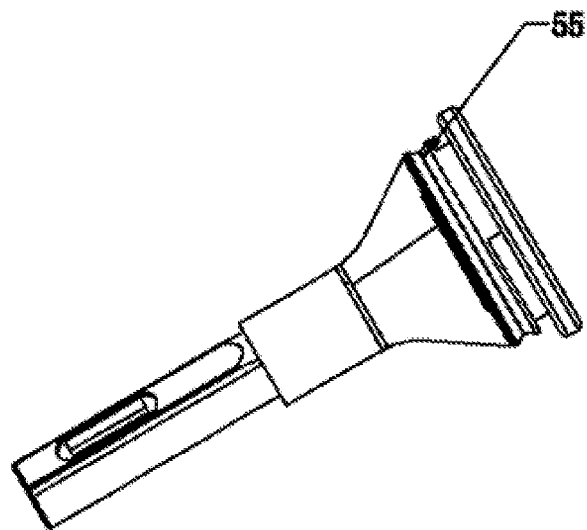
FIG. 4 is a structural diagram of the pedestal of the present application.

As shown in FIG. 4, the pedestal 12 is of a funnel shape having a central hole, the pedestal 12 comprises a top portion and a neck portion, and the top portion of the pedestal 12 is provided with a slot for mounting the lock buckle 11 and a groove for mounting the elastic rubber ring. The two sides of the slot are closed, to prevent the mismatching of the central hole of the lock buckle 11 and the hole within the pedestal 12, and the two ends of the slot are open, to enable the lock buckle 11 to reciprocate within the slot. The top portion of the central hole of the pedestal 12 is a connector for mounting the endoscope, the connector is provided with a hole therewithin, and a diameter of the hole is greater than a diameter of the endoscope, to facilitate the mounting.

The lock buckle 11 is mounted within the slot of the pedestal 12, and may reciprocate. The elastic rubber ring is mounted in the groove of the lock buckle 11 and the groove of the pedestal 12, so that the lock buckle 11 and the pedestal 12 are elastically connected. In the normal state, because the elastic rubber ring has elasticity, the step end of the lock buckle 11 is deviated from the central hole of the pedestal 12, the end that has the equal radius with the endoscope of the central hole of the lock buckle 11 coincides with the connector of the pedestal 12, the other end of the central hole of the lock buckle 11 is blocked by the tip of the pedestal 12. When the step end of the lock buckle 11 is being pressed, the end of the central hole of the lock buckle 11 that is greater than the radius of the endoscope coincides with the connector of the pedestal 12, and the other end of the central hole of the lock buckle 11 is blocked by the tip of the pedestal 12, at which time the endoscope can be installed.

When the endoscope is being installed, the step end of the lock buckle 11 is pressed, and the central hole on the lock buckle 11 that has the radius equal to that of the connector of the pedestal 12 coincides with the hole of the connector end of the pedestal 12, the endoscope is inserted into the lock buckle 11 and the pedestal 12, the step end of the lock buckle 11 is released, and because the elastic rubber ring has elasticity, the lock buckle 11 is repositioned, and the oblong hole of the lock buckle 11 with the radius equal to that of the endoscope clips the endoscope, and the endoscope is fixed.

In this embodiment, preferably, the radiuses of the oblong hole of the center of the lock buckle 11 are R6.2 mm and R5.3 mm, the total length of the oblong hole is 16.6 mm, the cross-section of the grooves on the lock buckle 11 and the pedestal 12 for mounting the elastic rubber ring are of a circular arc shape, the radius of the circular arc of the groove on the lock buckle 11 is R1 mm, and the radius of the circular arc of the groove on the pedestal 12 is R1.2 mm. The thickness of the lock buckle 11 is 1.2 mm, and the thickness of the slot for mounting the lock buckle on the pedestal 12 is 1.4 mm.

The pedestal 12 is fixedly connected to one end of the three-way connector 13 by a key slot and the locking screw 15.

Figure 5:
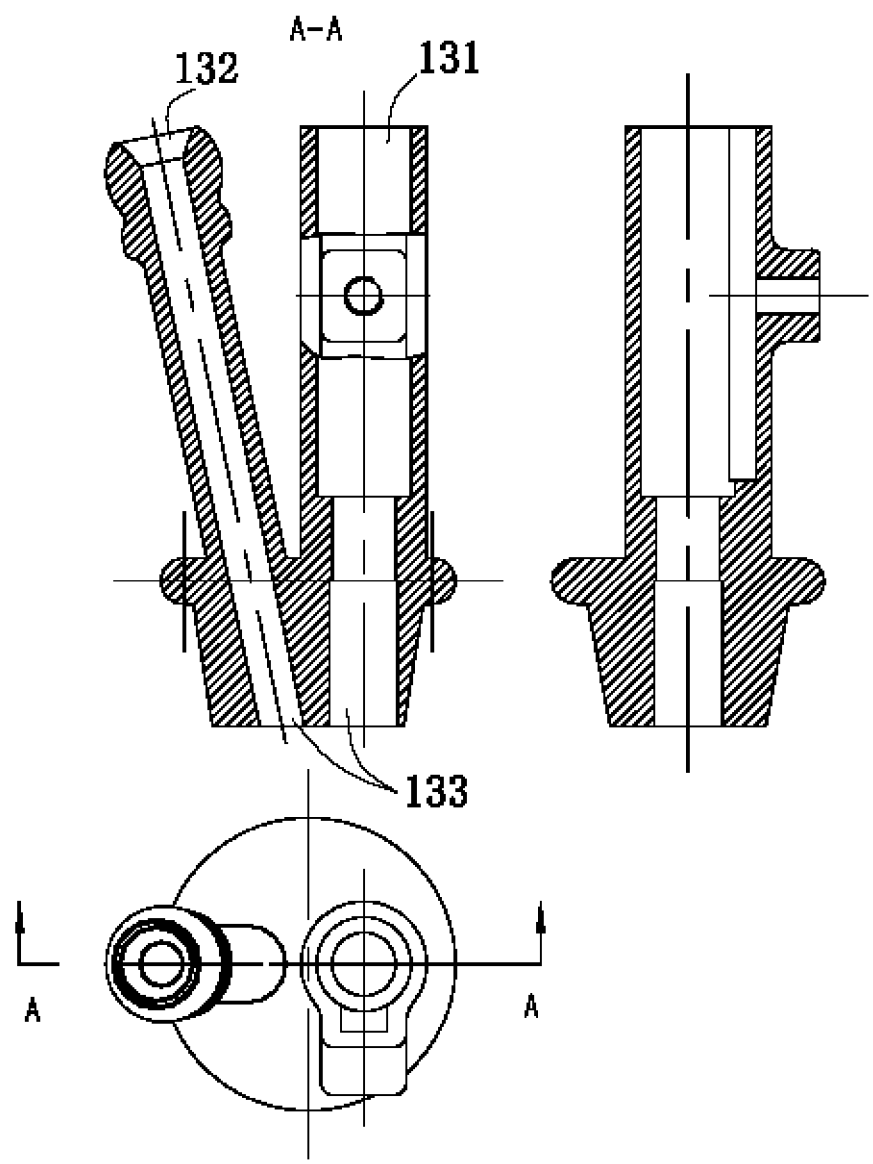
FIG. 5 is a structural diagram of the three-way connector of the present application.

As shown in FIG. 4, the neck portion of the pedestal 12 is a straight column section whose outer wall has a step, which can be very easily inserted into a through hole of the three-way connector 13. The outer wall surface of the straight column section is provided with a key-shaped protrusion, and the protrusion is provided with a rectangular slot, wherein the rectangular slot is for mounting the locking screw. As shown in FIG. 5, the three-way connector 13 is provided with three port ends, wherein the first connecting end 131 is connected to the pedestal 12. The first connecting end 131 is a straight column section whose interior has a two-section stepped hole and whose outer wall surface has a square tab. The first section of the stepped hole is an inner hole having a key slot, and the key slot is matched with the key-shaped protrusion of the pedestal. The inner diameter of the second section of the stepped hole is less than the inner diameter of the first section. The square tab is located on the outer wall corresponding to the key slot, the square tab is provided with a threaded through hole in the center, and the threaded through hole extends to the inner surface of the key slot, for mounting the locking screw.

The straight column section of the pedestal 12 is inserted into the first section of the stepped hole of the three-way connector 13, and the key slot is in clearance fit to the key-shaped protrusion, which facilitates the dismounting. The locking screw 15 passes through the threaded through hole of the tab of the three-way connector 13, and is screwed into the rectangular slot of the pedestal 12 tightly, whereby the pedestal 12 is fixed on the three-way connector 13. The rectangular slot of the pedestal 12 is of an elongated shape, and the locking screw 15 may be fixed at any position of the rectangular slot. When the position of the pedestal 12 is required to be changed, the locking screw 15 is unscrewed, the pedestal 12 is moved to the required position, and the locking screw 15 is screwed tightly again. In this way, although the dimensions of the pedestal 12 and the three-way connector 13 are not greatly changed, the position of the locking screw 15 in the rectangular slot can be varied according to the demands, to in turn vary the position of the pedestal 12. Such a variation of a small amplitude can hugely facilitate the practice operations.

As shown in FIG. 5, the second connecting end 132 of the three-way connector 13 is inclined by 12°, for the inserting of instruments such as surgical scissors. The third connecting end 133 of the three-way connector 13 directly communicates with the first connecting end 131, and the third connecting end 133 has a diameter greater than that of the second stepped section of the first connecting end 131. The third connecting end 133 of the three-way connector 13 is connected to the top of the four-way connector 14, the left and right ends of the four-way connector 14 are respectively connected to a water inlet pipe and a water outlet pipe, the water in the water inlet pipe enters a human body via the left end of the four-way connector 14, the contaminated water in the human body is discharged via the right end of the four-way connector 14, and the left and right ends of the four-way connector 14 are provided with through holes for mounting the valve 16, to control the connecting and breaking of the pipeline. The bottom end of the four-way connector 14 is connected to one end of the probe tube 17, and the other end of the probe tube 17 is connected to the probe head 18.

Figure 6:
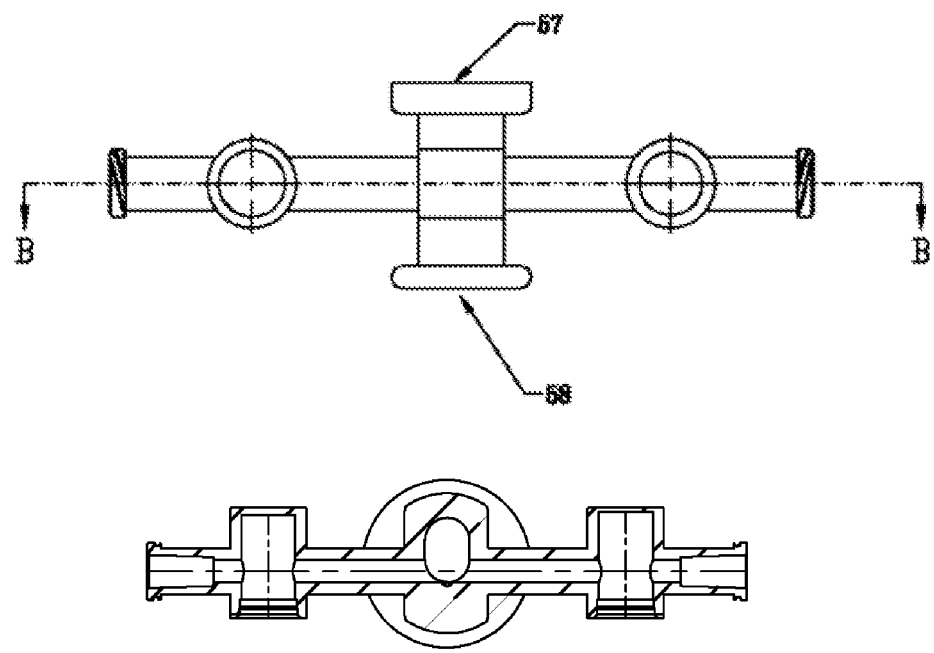
FIG. 6 is a structural diagram of the four-way connector of the present application.

As shown in FIG. 6, an oblong through hole is between the upper and lower ends of the four-way connector 14, and both of the left and right ends of the four-way connector 14 are provided with through holes, which communicate with one end of the oblong hole.

Figure 7:
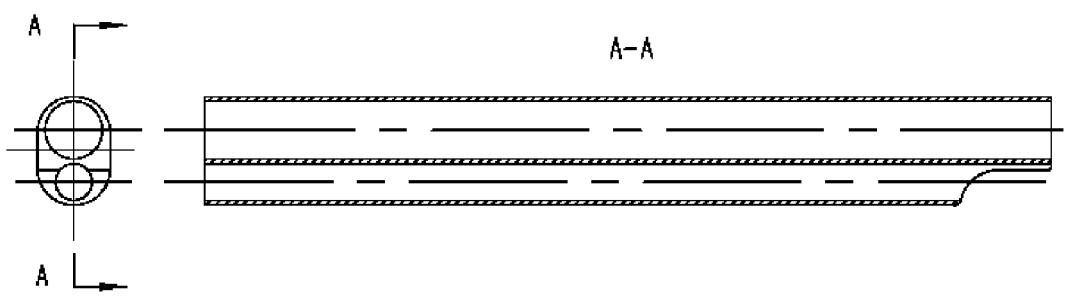
FIG. 7 is a schematic diagram of the mounting of the probe tube and the probe head of the present application.
Figure 8:
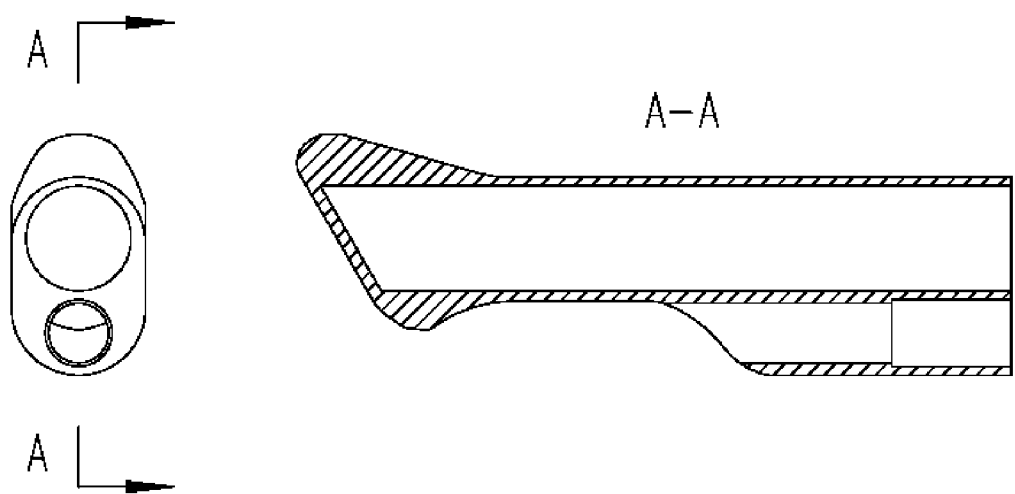
FIG. 8 is a structural diagram of the probe head of the present application.

As shown in FIG. 7, the probe tube 17 is a long-cylinder-shaped straight tube, with a cross-section of an oblong shape, and comprises two straight through round holes, one with a larger diameter and the other one with a smaller diameter, and the two straight through round holes do not communicate.

The probe head 18 is a long-cylinder-shaped straight tube, and comprises two straight through round holes, one with a larger diameter and the other one with a smaller diameter. The front end of the straight through round hole with the larger diameter is inclined by 60°, and the inclining position is provided with a transparent viewing window. The round hole with the larger diameter is closed by the transparent viewing window, and the transparent viewing window facilitates the observation with the endoscope. The tip of the straight through round hole with the larger diameter is a round tip with a circular arc transition, whereby the sheath can be conveniently inserted into a human body, and not cause scratching. The length of the round hole with the smaller diameter is shorter than the length of the round hole with the larger diameter, and the tip of the straight through round hole with the smaller diameter is inclined by 60°.

The thick pipe 19 is mounted within the round tube with the larger diameter of the probe tube 17, and the thin pipe 20 is mounted within the round tube with the smaller diameter. One end of the thick pipe 19 is inserted into the round tube with the larger diameter of the probe head 18 via the probe tube 17, and is fixedly connected to the probe head, and the other end of the thick pipe 19 is inserted into the first section of the stepped hole of the first connecting end 131 of the three-way connector 13 via an oblong through hole of the four-way connector 14. The inner diameter of the second section of the stepped hole of the first connecting end 131 is less than the external diameter of the thick pipe 19, so that the thick pipe 19 and the first connecting end 131 are connection of interference fit, whereby the probe head 18 is fixed to the probe tube 17 via the thick pipe 19. The thin pipe 20 is mounted within one end of the oblong hole of the four-way connector 14, and the end of the oblong hole is adjacent to the left and right through holes, the thin pipe 20 communicate with the left and right through holes, and the thick pipe 19 is mounted at the other end of the oblong hole. The thin pipe 20 is mounted within the round hole with the smaller diameter of the probe tube, wherein one end is fixed to the oblong through hole of the four-way connector 14, and communicates with the through holes of the left and right ends of the four-way connector 14, and the other end is inserted into the probe head 18.

One end of the thick pipe 19 is fixed within the round hole with the larger diameter of the probe head 18. The probe tube 17, the four-way connector 14 and the thick pipe 19 are in clearance fit, to enable the thick pipe 19 to be very easily drawn from the round hole. The thick pipe 19 is in interference fit to the first connecting end 131 of the three-way connector 13, whereby the thick pipe 19 does not fall freely during usage. The outer surface of the thick pipe 19 is printed with a plurality of strip-shaped metal round rings, to increase the friction between the thick pipe 19 and the inner wall of the probe tube 17, and to prevent the thick pipe 19 from falling in the process of drawing the thick pipe 19.

Endoscope sheaths are generally formed by extrusion integrally. The manufacturing process cannot ensure the finish degree of the inner surface of the probe tube 17, and if the inner surface is further processed, the cost of the process is too high. Moreover, both of the thick pipe 19 and the thin pipe 20 are made from stainless steel, which can ensure the straightness and smoothness of the inner wall, and has the advantages of a high strength and a high rigidity. When the thick pipe 19 and the thin pipe 20 are mounted within the probe tube, the rigidity and strength of the probe tube can be significantly increased, and the probe tube does not easily bend and transform in the process of the insertion into a human body and does not easily fall in the process of a surgery.

On the basis of the above structures, the second connecting end 132 of the three-way connector 13, the four-way connector 14, the thin pipe 20 within the round hole with the smaller diameter of the probe tube 17 and the probe head 18 form an instrument channel, for delivering the instrument into a human body in the process of a surgery for operation, and the lock buckle 11, the pedestal 12, the first connecting end 131 of the three-way connector 13 and the thick pipe 19 form an endoscope channel, for delivering the endoscope to the site to be observed.

Because the probe head 18 is provided with the transparent viewing window at the tip, the endoscope does not contact with the human body or any liquid, which ensures the cleanness of the endoscope. By using the valve 16 on the four-way connector 14, external water can enter the human body via the instrument channel, and then the contaminated water can be discharged via the instrument channel through the valve 16.

In usage, firstly the sheath is inserted into the human body, a water inlet pipeline and a water outlet pipeline are respectively connected to a connecting end 57 of the four-way connector 14 and another connecting end 58 of the four-way connector 14, the valve 16 connected to the water outlet pipeline is shut, the valve 16 connected to the water inlet pipeline is opened, the water enters the human body via the instrument channel, then the valve 16 connected to the water inlet pipeline is shut, the valve 16 connected to the water outlet pipeline is opened, and the contaminated water is discharged. The lock buckle cap 21 on the lock buckle 11 is pressed, to coincide the central hole on the lock buckle 11 that has the radius equal to that of the connector of the pedestal 12 and the hole of the connector end of the pedestal 12, the tip of the endoscope is inserted into the thick pipe 19, the transparent viewing window is used for observation, the step end of the lock buckle 11 is released, the lock buckle 11 is repositioned by the elasticity of the elastic rubber ring, and the end of the oblong hole with the radius equal to that of the endoscope clips the endoscope, and the endoscope is fixed. The instrument such as medical scissors enters the four-way connector 14 and the thin pipe 20 via the second connecting end 132 of the three-way connector 13, and passes through the probe head 18 into the human body for operation.

After the surgery has ended, the step end of the lock buckle 11 is pressed, to coincide the central hole on the lock buckle 11 that has the radius equal to that of the connector of the pedestal 12 and the hole of the connector end of the pedestal 12, the endoscope is taken out, the instrument is taken out at the same time, and the sheath is taken out of the human body. Because the endoscope did not contact with the human body or other liquids, the endoscope can be used for a next surgery after merely a simple disinfection, which is convenient.

In conclusion, the present application provides an endoscope locking device, which fixes the endoscope by using the elasticity of the elastic rubber ring to the endoscope locking device formed by the lock buckle and the pedestal. The device has a simple structure, and the assembling and detaching of the endoscope are simple, which can improve the surgery efficiency.

The above are merely preferable particular embodiments of the present application, and the protection scope of the present application is not limited thereto. All of the variations or substitutions that a person skilled in the art can easily envisage within the technical scope disclosed by the present application should fall within the protection scope of the present application.

What is claimed is:

1. An endoscope locking device, comprising: a pedestal, a lock buckle and an elastic element;
   wherein the pedestal is provided with a slot, and the slot is configured to mount the lock buckle, the lock buckle is provided with an oblong hole in a center, and the lock buckle is mounted within the slot of the pedestal, and the lock buckle reciprocates within the slot; and
   wherein the elastic element is configured to elastically connect the lock buckle and the pedestal;
   wherein the elastic element is an elastic rubber ring;
   wherein the pedestal is provided with a groove for mounting the elastic rubber ring;
   wherein one end of the lock buckle is a step having a circular arc transition, the other end is a circular arc, the circular arc end is provided with a protrusion, and the protrusion is provided with a groove for mounting the elastic rubber ring;
   wherein the elastic rubber ring is mounted in the groove of the lock buckle and the groove of the pedestal, and the lock buckle and the pedestal are elastically connected;
   wherein a lock buckle cap is mounted on the step of the lock buckle, for pressing the lock buckle, to facilitate the operation.

2. The endoscope locking device according to claim 1, wherein the slot of the pedestal is closed at two sides and is open at two ends.

3. The endoscope locking device according to claim 2, wherein a radius of one end of the oblong hole of the center of the lock buckle is equal to a radius of an endoscope, and a radius of the other end is greater than the radius of the endoscope.

4. The endoscope locking device according to claim 1, wherein the lock buckle is of a cuboidal sheet structure.

5. The endoscope locking device according to claim 1, wherein the pedestal is of a funnel shape having a central hole, the pedestal comprises a top portion and a neck portion, the top portion of the central hole of the pedestal is a connector for mounting the endoscope, the connector is provided with a round hole therewithin, and a diameter of the round hole is greater than a diameter of the endoscope.

6. An endoscope sheath, comprising an endoscope locking device, a three-way connector, a four-way connector, a locking screw, a valve, a probe tube, a probe head, a first pipe, a second pipe and a lock buckle cap;
   wherein the endoscope locking device comprises: a pedestal, a lock buckle and an elastic element; the pedestal is provided with a slot, and the slot is configured to mount the lock buckle, the lock buckle is provided with an oblong hole in a center, and the lock buckle is mounted within the slot of the pedestal, and the lock buckle reciprocates within the slot;

the elastic element is configured to elastically connect the lock buckle and the pedestal;

wherein the elastic element is an elastic rubber ring;

wherein the pedestal is provided with a groove for mounting the elastic rubber ring;

wherein one end of the lock buckle is a step having a circular arc transition, the other end is a circular arc, the circular arc end is provided with a protrusion, and the protrusion is provided with a groove for mounting the elastic rubber ring;

wherein the elastic rubber ring is mounted in the groove of the lock buckle and the groove of the pedestal, and the lock buckle and the pedestal are elastically connected;

wherein a lock buckle cap is mounted on the step of the lock buckle, for pressing the lock buckle, to facilitate the operation;

and the endoscope locking device is connected to a first connecting end of the three-way connector, a second connecting end of the three-way connector is an instrument entrance, a third connecting end of the three-way connector is connected to a connecting end of the four-way connector, one end of the probe tube is connected to another connecting end of the four-way connector, and the probe head is connected to the other end of the probe tube.

* * * * *